United States Patent [19]

Ford et al.

[11] Patent Number: 4,827,041

[45] Date of Patent: May 2, 1989

[54] PROCESS FOR THE MANUFACTURE OF 1,4-BIS(4-PHENOXYBENZOYL)BENZENE WITH A PERFLUOROSULFONYL RESIN CATALYST

[75] Inventors: Thomas M. Ford, Greenville; Enio Kumpinsky; Antonio Vidal, both of Wilmington, all of Del.

[73] Assignee: E. I. Du Pont de Nemours and Company, Wilmington, Del.

[21] Appl. No.: 166,485

[22] Filed: Mar. 10, 1988

[51] Int. Cl.[4] .............................................. C07C 45/46
[52] U.S. Cl. ..................................................... 568/322
[58] Field of Search ........................ 568/319, 322, 323

[56] References Cited

U.S. PATENT DOCUMENTS

| | | | |
|---|---|---|---|
| 3,907,837 | 9/1975 | Effenberger et al. | 568/323 |
| 4,052,401 | 10/1977 | Hughes | 260/340.7 |
| 4,053,522 | 10/1977 | McClure et al. | 260/619 A |
| 4,306,094 | 12/1981 | Shozda | 568/637 |
| 4,396,755 | 8/1983 | Rose | 528/126 |
| 4,423,252 | 12/1983 | Maki et al. | 568/728 |
| 4,478,956 | 10/1984 | Maki et al. | 521/32 |
| 4,487,934 | 12/1984 | Shutske et al. | 546/314 |

*Primary Examiner*—James H. Reamer
*Attorney, Agent, or Firm*—Paul R. Steyermark

[57] ABSTRACT

A process for manufacturing 1,4-bis(4-phenoxybenzoyl)benzene, wehrein diphenyl ether is contacted for about 30–360 minutes at 130°–200° C. with 1,4-benzenedicarbonyl chloride in respective mole ratios of about 15–80:1 in the presence of a fluorocarbon resin carrying pendant sulfonic acid groups, the weight ratio of the resin to 1,4-benzenedicarbonyl chloride being 3:1–1:2; the hot solution is separated from the resin, and the crystalline product is recovered from the solution on cooling. The so obtained 1,4-bis(4-phenoxybenzoyl)benzene is a high purity material free of ortho-isomer and catalyst contamination and can be used without further purification as one of the starting materials in the preparation of polyetherketones, which are important engineering resins.

9 Claims, No Drawings

PROCESS FOR THE MANUFACTURE OF 1,4-BIS(4-PHENOXYBENZOYL)BENZENE WITH A PERFLUOROSULFONYL RESIN CATALYST

BACKGROUND OF THE INVENTION

This invention relates to a process for the manufacture of 1,4-bis(4-phenoxybenzoyl)benzene (sometimes referred to hereinafter as BPBB) in a hetereogeneous system, in the presence of a perfluorosulfonyl resin catalyst, which can be readily separated from the liquid phase in the reaction mixture.

BPBB, which is an important intermediate in the preparation of polyetherketone resins, can be made by condensation of 1,4-benzenedicarbonyl chloride with diphenyl ether in the presence of a Friedel-Crafts catalyst, usually aluminum chloride, which is employed in an amount of at least three moles per mole of 1,4-benzenedicarbonyl chloride. Diphenyl ether normally is used in a significant excess to minimize formation of higher oligomers. Normally, the reaction is carried out in a solvent such as, e.g., 1,2-dichlorobenzene, at a temperature of approximately $-10°$ C. After the reaction is complete, methanol is added to precipitate the product and remove aluminum chloride therefrom. The product is filtered off, washed repeatedly with methanol, and recrystallized from N,N-dimethylacetamide.

Use of aluminum chloride catalyst presents various shortcomings. Aluminum chloride, which is soluble in hot 1,2-dichlorobenzene, tends to contaminate the BPBB product, thus requiring repeated washings for its removal from the product and finally recrystallization of BPBB. The recovered aluminum chloride cannot be reused and this creates a waste disposal problem as well as adds to the cost of the operation. Finally, aluminum chloride does not have a high para-isomer selectivity, so that it tends to also produce a fair proportion of the ortho-isomer, i.e., 1,4-bis(2-phenoxybenzoyl)benzene or mixed isomer.

It would be desirable to be able to produce BPBB in a simpler operation, which would result in a good yield of a high purity material free of ortho-isomer and catalyst contamination, so that the additional purification steps could be avoided, and the overall reaction yield could be increased.

SUMMARY OF THE INVENTION

According to this invention, there is now provided a process for the manufacture of 1,4-bis(4-phenoxybenzoyl)benzene, said process comprising contacting diphenyl ether for a period of about 30–360 min at a temperature of about 130°–200° C. with 1,4-benzenedicarbonyl chloride in respective mole ratios of about 15–80:1 in the presence of a fluorocarbon resin carrying pendant sulfonic acid groups, the weight ratio of 1,4-benzenedicarbonyl chloride to the resin being about 3:1 to 1:2, separating the resulting hot solution from the resin, cooling the hot solution to a temperature at which 1,4-bis(4-phenoxybenzoyl)benzene crystallizes, and separating the crystalline product from the cooled solution.

DETAILED DESCRIPTION OF THE INVENTION

The basic reaction involved in the process of this invention is shown in the following equation:

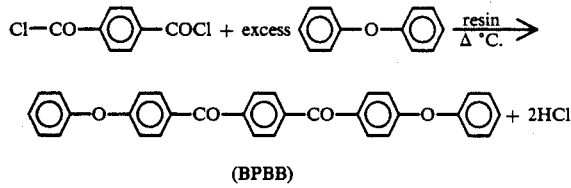

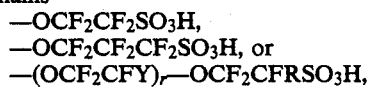

(BPBB)

The starting materials for this reaction are well known and readily available.

1,4-Benzenedicarbonyl chloride, also known as terephthalyl chloride, can be made from terephthalic acid by any suitable known reaction, e.g., with phosphorus pentachloride, phosphorus trichloride, or thionyl chloride. 1,4-Benzenedicarbonyl chloride also is commercially available, i.a., from E. I. du Pont de Nemours and Company.

Diphenyl ether is commercially available, i.a., from Dow Chemical Company.

Fluorocarbon resins carrying pendant sulfonic acid groups, which are suitable as the reaction catalyst, are well known commercial products available, i.a. from E. I. du Pont de Nemours and Company, under the trademark Nafion ®. The usual commercial resin is a copolymer of tetrafluoroethylene with at least one other ethylenically unsaturated fluoro comonomer and has a pendant sulfonyl group $-SO_3H$. Most preferred fluorocarbon resins carrying pendant sulfonic acid groups have a number average molecular weight of at least about 5,000. Preferably, the resin contains a sufficient number of sulfonic acid groups to give an equivalent weight of from about 500 to about 20,000, especially from about 900 to about 2,000. Although the polymer backbone comprises, for the most part, fluorinated carbon atoms, it is not necessary that all other atoms be excluded. For example, ether oxygen atoms may be present in the backbone as well as in the side chains of the polymer. Such other atoms and/or groups as hydrogen, chlorine, and carboxyl may be present in limited amounts without affecting the stability or operability of the polymer under the process conditions. It is preferred that the total amount of hydrogen and chlorine not exceed about 5 weight percent of the resin. Typical sulfonic acid group-containing resins which can be used in the process of the present invention are described, for example, in U.S. Pat. Nos. 3,718,627 (Grot) and 3,282,875 (Connolly et al. Du Pont). Representative copolymers suitable as catalysts according to the process of the present invention may contain, for example, the side chains $-OCF_2CF_2SO_3H$, $-OCF_2CF_2CF_2SO_3H$, or $-(OCF_2CFY)_r-OCF_2CFRSO_3H$, where Y is F or $CF_3$; R is F, Cl, $CF_2Cl$, or a $C_1$ to $C_{10}$ perfluoroalkyl radical; and r is 0, 1, 2, or 3. Since these resins can exist either in their acid form, where their $-SO_3H$ group is not neutralized, or in a salt form, where the hydrogen of the sulfonyl group is replaced by a cation (e.g., a metal ion such as sodium or potassium), it is important to keep in mind that the resin catalyst according to the process of the present invention is used in its acid (hydrogen ion) form.

In the practical operation of this invention, the reactants and the resin catalyst are charged into the reactor, and the temperature is raised to the desired range either at atmospheric pressure or at a reduced pressure.

While a large excess of diphenyl ether is necessary, it is preferred to keep the diphenyl ether/1,4-benzendicarbonyl chloride mole ratio within the range of 40-50:1. The preferred reaction temperature is 150°-170° C. Within this temperature range, the preferred reaction time is about 40-60 min. The most preferred reaction conditions are 40 minutes at 160° C. and at 27 kPa pressure. Generally, if the process temperature is too low, conversion of the starting materials to the desired product, BPBB, will be reduced below a commercially attractive level. If the temperature is too high, the catalyst becomes thermally unstable, and impure BPBB is made.

BPBB, which crystallizes from the solution in diphenyl ether after cooling, is of sufficiently high purity to be used without recrystallization for the final step of making a polyetherketone by condensation with additional 1,4-benzenedicarbonyl chloride (or another dicarboxylic acid dichloride) in a manner known to the art. The preferred temperature to which the solution is cooled and at which BPBB is isolated is about 25°-40° C.

Excess diphenyl ether can be reused several times without purification. When purification is deemed advisable, this is done most conveniently by distillation at a reduced pressure.

The perfluorosulfonyl resin catalyst can be recovered and regenerated, e.g., by heating for several hours under reflux with 1-pentanol, soaking in methanol, and drying.

While the above description concerns a batch process of this invention, the process can be adapted to a continuous operation, where the critical variables to be controlled are the weight ratio of 1,4-benzenedicarbonyl chloride to resin material, the mole ratio of diphenyl ether to 1,4-benzenedicarbonyl chloride, temperature, and residence time. Various routine operations can be modified in both the batch process and the continuous process so as to obtain the greatest operational efficiency; e.g. separation of solids from liquids can be achieved not only by filtration but also by decantation or centrifugation, whichever is the most convenient, i.a., from the standpoint of time, energy requirement, and equipment available.

This invention is now illustrated by representative examples of certain preferred embodiments thereof. In all the examples, the conversion of 1,4-benzenedicarbonyl chloride to BPBB was calculated as follows:

$$\text{conversion (\%)} = \frac{\text{moles of BPBB in the product}}{\text{moles of 1,4-benzenedicarbonyl chloride in the feed}} \times 100$$

Any partial reaction product, comprising 1 molecule of each reactant, that may have been formed as a side product was disregarded.

EXAMPLE 1

A charge of 134 g of diphenyl ether was heated in a reactor to 140° C. Perfluorosulfonyl resin, 1.22 g, which was a copolymer of tetrafluoroethylene with perfluoro(3,6-dioxa-4-methyl-7-octene)sulfonic acid, and had a sulfonyl group concentration of 0.8 milliequivalents per gram (meq/g) sized between 75 and 150 micrometers, previously dried by heating for one hour at 100° C., was added to the reactor. The mixed charge was heated to 180° C. and 3 g of 1,4-benzenedicarbonyl chloride was added. The reactor charge was maintained at 180° C. with agitation for 6 hours; it was then filtered hot to separate the solution from the resin, and the filtrate was cooled to room temperature. Solid BPBB, which crystallized from the solution on cooling, was recovered by filtration. The conversion of 1,4-benzendicarbonyl chloride to BPBB was 64%.

EXAMPLE 2 (COMPARATIVE)

The process of Example 1 was repeated, except that 1,3-benzenedicarbonyl chloride was substituted for 1,4-benzenedicarbonyl chloride, and the reaction time was 4 hours, rather than 6. No condensation product was obtained. This example shows that catalysis by perfluorosulfonyl resin is para,para-specific.

EXAMPLE 3

This experiment was run in a 380 L reactor. A total of 283.5 kg of diphenyl ether was charged to the reactor at 40° C.. After the temperature was raised to 120° C., 6.35 kg of 1,4-benzenedicarbonyl chloride was added. The temperature was further increased to 160° C., and 12.70 kg of perflurosulfonyl resin (same as in Example 1) having a particle size of less than 500 micrometers was charged to the reactor. The reaction was allowed to proceed for 40 minutes under a nitrogen purge and at a pressure of 27 kPa. The resin catalyst was filtered off at 160° C., following which the filtrate was allowed to cool down. BPBB began to crystallize out of the solution at about 120° C.; it was recovered by filtration at 40° C., washed with methanol and with tetrahydrofuran, and dried. The dry product weighed 6.33 kg, corresponding to a yield of 43%.

EXAMPLE 4

A total of 40 g of perfluorosulfonyl resin recovered from Example 3 was refluxed for 6 hours in 1-pentanol. This recovered resin was then soaked for 16 hours in methanol; it was filtered and dried for 20 hours at 110° C. in a vacuum oven with a nitrogen purge.

The resin was reused as follows. Diphenyl ether, (895 g) was charged into a 2 L reactor and heated to 120° C., at which point 20 g of 1,4-benzenedicarbonyl chloride was added. The temperature was increased to 160° C., whereupon the recovered and regenerated resin was charged to the reactor. The charge was heated for 40 minutes under a nitrogen purge, at a pressure of 27 kPa. The perfluorosulfonyl resin was filtered off at 160° C. from the diphenyl ether solution, and the filtrate was allowed to cool to 30° C. BPBB, which precipitated on cooling, was recovered by filtration and dried for 64 hours with a nitrogen purge in a vacuum oven at 110° C. The yield of the dry BPBB was 21.3 g (46% conversion).

We claim:

1. A process for the manufacture of 1,4-bis(4-phenoxybenzoyl)benzene, said process comprising contacting diphenyl ether for a period of about 30-360 min at a temperature of about 130°-200° C. with 1,4-benzenedicarbonyl chloride in respective mole ratios of about 15-80:1 in the presence of a resin which is a copolymer of tetrafluoroethylene with at least one other ethylenically unsaturated comonomer, said resin carrying a sufficient number of pendant sulfonic acid groups, which may be attached to side chains, to give an equivalent weight of from about 500 to about 20,000, ether oxygen atoms as well as additional atoms or groups, especially hydrogen, chlorine, and carboxyl groups, being permitted both in the fluorocarbon backbone and in the side chains to the extent that they do not adversely affect the stability and operability of the resin under process conditions, the total amount of hydrogen and chlorine, if present, not exceeding about 5 weight percent of the resin, the weight ratio of 1,4-benzenedicarbonyl chloride to the resin being about 3:1 to 1:2, separating the resulting hot solution from the resin, cooling the hot solution to a temperature at which 1,4-bis(4-phenoxybenzoyl)benzene crystallizes, and separating the crystalline product from the cooled solution.

2. The process of claim 1 wherein the mole ratio of diphenyl ether to 1,4-benzenedicarbonyl chloride is 40–50:1.

3. The process of claim 2 wherein the reaction temperature is 150°–170° C.

4. The process of claim 3 wherein the reaction time is 40–60 minutes.

5. The process of claim 4, which is carried out for about 40 minutes at about 160° C. and at a pressure of about 27 kPa.

6. The process of claim 1 wherein the temperature to which the solution is cooled before the product is isolated is about 25°–40° C.

7. The process of claim 1 wherein the number of sulfonic groups is such that the equivalent weight of the resin is about 900 to about 2000.

8. The process of claim 1 wherein the fluorocarbon resin contains side chains represented by at least one of the following formulas:
—$OCF_2CF_2SO_3H$,
—$OCF_2CF_2CF_2SO_3H$, or
—$(OCF_2CFY)_r$—$OCF_2CFRSO_3H$,
where Y is F or $CF_3$; R is F, Cl, $CF_2Cl$, or a $C_1$ to $C_{10}$ perfluoroalkyl radical; and r is 0, 1, 2, or 3.

9. The process of claim 8, wherein the number of sulfonic groups is such that the equivalent weight of the resin is about 900 to about 2000.

* * * * *